United States Patent
Manigel et al.

(10) Patent No.: US 6,651,657 B1
(45) Date of Patent: Nov. 25, 2003

(54) RESPIRATOR FOR DIFFERENT FORMS OF RESPIRATION

(75) Inventors: Jürgen Manigel, Klingberg (DE); Thomas Simmerer, Krummesse (DE)

(73) Assignee: Dräger Medizintechnik GmbH, Lübeck (DE)

( * ) Notice: Subject to any disclaimer, the term of this patent is extended or adjusted under 35 U.S.C. 154(b) by 0 days.

(21) Appl. No.: 09/551,052

(22) Filed: Apr. 18, 2000

(30) Foreign Application Priority Data

Dec. 18, 1999 (DE) .......................................... 199 61 253

(51) Int. Cl.⁷ ............................................. A61M 16/00
(52) U.S. Cl. ............................... 128/204.21; 128/204.18
(58) Field of Search ....................... 128/200.24, 204.18, 128/204.21, 204.22, 204.23, 204.26, 203.12, 203.14, 207.14, 205.18; 600/529, 533, 538

(56) References Cited

U.S. PATENT DOCUMENTS

| | | | | | |
|---|---|---|---|---|---|
| 3,961,627 A | * | 6/1976 | Ernst et al. | ............. | 128/202.22 |
| 4,036,221 A | * | 7/1977 | Hillsman et al. | ...... | 128/204.23 |
| 4,448,192 A | * | 5/1984 | Stawitcke et al. | ..... | 128/204.21 |
| 4,661,092 A | * | 4/1987 | Popovich et al. | ............. | 422/45 |
| 4,838,257 A | * | 6/1989 | Hatch | ............. | 128/204.18 |
| 4,957,107 A | * | 9/1990 | Sipin | ............. | 128/204.21 |
| 5,107,830 A | * | 4/1992 | Younes | ............. | 128/204.18 |
| 5,129,390 A | * | 7/1992 | Chopin et al. | ......... | 128/204.21 |
| 5,316,009 A | * | 5/1994 | Yamada | ............. | 128/716 |
| 5,497,767 A | * | 3/1996 | Olsson et al. | ........... | 128/205.13 |
| 5,575,283 A | * | 11/1996 | Sjoestrand | ............. | 128/204.18 |
| 5,694,926 A | * | 12/1997 | DeVries et al. | ........ | 128/204.21 |
| 5,797,393 A | * | 8/1998 | Kohl | ..................... | 128/204.18 |
| 5,868,133 A | * | 2/1999 | DeVries et al. | ........ | 128/204.18 |
| 5,875,777 A | | 3/1999 | Eriksson | | |
| 5,975,078 A | * | 11/1999 | Pauley | .................. | 128/203.12 |
| 6,029,664 A | * | 2/2000 | Zdrojkowski et al. | . | 128/204.23 |
| 6,123,072 A | * | 9/2000 | Downs | .................. | 128/204.21 |
| 6,131,571 A | * | 10/2000 | Lampotang et al. | ... | 128/204.21 |
| 6,152,132 A | * | 11/2000 | Psaros | .................... | 128/200.24 |
| 6,158,430 A | * | 12/2000 | Pfeiffer et al. | ......... | 128/202.27 |
| 6,220,245 B1 | * | 4/2001 | Takabayashi et al. | .. | 128/202.12 |
| 6,240,920 B1 | * | 6/2001 | Strom | .................... | 128/204.23 |
| 6,244,267 B1 | * | 6/2001 | Eifrig | .................... | 128/202.22 |
| 6,250,302 B1 | * | 6/2001 | Rantala | ................. | 128/204.21 |
| 6,257,234 B1 | * | 7/2001 | Sun | ....................... | 128/204.18 |
| 6,260,550 B1 | * | 7/2001 | Weismann et al. | ..... | 128/203.25 |
| 6,369,838 B1 | * | 4/2002 | Wallace et al. | ........ | 128/204.18 |
| 6,422,237 B1 | * | 7/2002 | Engel et al. | ........... | 128/204.18 |

\* cited by examiner

*Primary Examiner*—Weilun Lo
*Assistant Examiner*—Teena Mitchell
(74) *Attorney, Agent, or Firm*—McGlew and Tuttle, P.C.

(57) ABSTRACT

A respirator for supplying a patient with breathing is provided such that the respiration will not be compromised at the time of a changeover from one form of respiration to another form of respiration. Provisions are made for carrying out a first form of respiration with the corresponding first setting parameters and for taking over the corresponding setting parameters at least partially from the measured values determined during the first form of respiration and the first respiration parameters that remained invariant at the time of the changeover of the forms of respiration at the time of a changeover to a second form of respiration.

26 Claims, 2 Drawing Sheets

RESPIRATOR FOR DIFFERENT FORMS OF RESPIRATION

FIELD OF THE INVENTION

The present invention pertains to a respirator for supplying a patient with breathing gas and to a process for controlling the respirator.

BACKGROUND OF THE INVENTION

A respirator, with which both mechanical and manual respiration can be performed, has been known from U.S. Pat. No. 5,875,777. To adapt the mechanical respiration to the breathing pattern of manual respiration as closely as possible, certain parameters of respiration, such as the breathing gas flow, the airway pressure and the duration of inspiration and expiration are measured and stored. The manual respiration is reproduced during the mechanical respiration on the basis of these data. To eliminate stochastic fluctuations, the measured values obtained during the manual respiration are evaluated over a larger number of breathing cycles in order to then form mean values.

Respirators used in anesthesia or intensive care offer a large number of forms of mechanical respiration, besides the purely manual respiration, in order to optimally supply the patient with breathing air. These forms of respiration are controlled either purely by the pressure or purely by the volume, and numerous mixed forms between volume-controlled and pressure-controlled respiration are used as well. The problem faced by the user is not only to carry out the changeover from manual respiration to mechanical respiration possibly without a transition, but also to carry out the changeover between the mechanical forms of respirations such that the time of the changeover will not be perceived by the patient. To achieve this, setting parameters that are needed for the new form of respiration but are inactive during the current form of respiration must be set as adequately as possible.

SUMMARY AND OBJECTS OF THE INVENTION

The primary object of the present invention is to improve a respirator such that the respiration is not compromised during the changeover from one form of respiration to another form of respiration and to provide a process for controlling the respirator.

According to the invention, a respirator is provided with a volume-shifting device, which is designed to carry out preselected forms of respiration. A gas line system is connected to the volume-shifting device for supplying a patient with breathing gas. Measuring devices are provided for at least the airway pressure and the breathing gas flow, wherein at least a plateau pressure $P_{plat}$ and a said inspiratory volume $V_T$ are determined as measured values. A control unit is provided which contains an input unit for setting at least a first form of respiration and a second form of respiration as well as for entering at least first setting parameters belonging to the first form of respiration. The control unit generates control signals for at least the volume-shifting device in order to carry out the first form of respiration with the first setting parameters. The control unit is designed such that at the time of a changeover to the second form of respiration, the corresponding setting parameters are selected at least partially from among the measured values determined during the first form of respiration and they are taken over as second setting parameters for the second form of respiration.

According to another aspect of the invention, a respirator is provided containing a volume-shifting device. The respirator is designed to carry out preselected forms of respiration. A gas line system is connected to the volume-shifting device for supplying a patient with breathing gas. A manual respiration device is connected to the gas line system. Measuring devices for at least the airway pressure, the breathing gas flow and the breathing time are provided. At least a plateau pressure $P_{plat}$, an inspiratory volume $V_T$, an inspiration time $T_i$ and a expiration time $T_e$ are determined as measured values. A control unit is provided, which contains an input unit for setting a manual form of respiration and a mechanical form of respiration with corresponding setting parameters. The control unit generates control signals for the volume-shifting device during the mechanical form of respiration in order to carry out the respiration with the setting parameters. The measured values determined during the manual form of respiration for the inspiration time $T_i$, expiration time $T_e$ and the plateau pressure $P_{plat}$ are taken over as setting parameters.

According to another aspect of the invention, a process for controlling a respirator, is provided wherein the respirator has a volume-shifting device for carrying out preselected forms of respiration. A gas line system is connected to the volume-shifting device for supplying a patient with breathing gas. Measuring devices are provided for at least the airway pressure $P_{aw}$ and the breathing gas flow, wherein at least a said plateau pressure $P_{plat}$ and a said inspiratory volume $V_T$ are determined as measured values. A first form of respiration is carried out with first setting parameters. The measured values, $P_{plat}$ or $V_T$, which are not first setting parameters, are determined during the first form of respiration. At the time of a changeover to a second form of respiration, the corresponding setting parameters are selected at least partially from among the measured values determined during the first form of respiration and are taken over as second setting parameters for the second form of respiration.

The advantage of the present invention is essentially that the setting parameters for mechanical forms of respiration that are not active during a form of respiration being currently performed but are needed for carrying out another form of respiration are determined as measured values during the form of respiration currently being set and these are taken over as setting parameters at the time of the changeover to a new form of respiration.

To carry out a first form of respiration in the respirator described in the present invention, first setting parameters are entered via the input unit into the control device. The volume-shifting device receives corresponding control signals from the control unit in order to carry out the first form of respiration. Discrete measured values, e.g., the plateau pressure $P_{plat}$, the inspiratory volume $V_T$, or the mean inspiratory flow $V_{insp}$, determined as a volume per unit of time, are determined with the measuring devices present in the breathing circuit for the breathing gas flow and the airway pressure.

At the time of the changeover to a second form of respiration, which has second setting parameters, the second setting parameters are taken over partially or even completely from the discrete measured values determined during the first form of respiration and, if possible, from the first setting parameters. Before the respiration with the second setting parameters is carried out, these are first displayed once again to the user, so that he can check them and take them over by actuating an acknowledge button.

The volume-shifting device needed to carry out mechanical respiration may have various designs. Usual embodiments are a bellows pump, a blower in the form of a radial flow compressor, or even a controllable metering valve, which is arranged downstream of a pressurized gas tank filled with breathing gas.

It is expedient to set certain setting parameters as fixed parameters on an input unit and to adapt other setting parameters in a need-adapted manner. Fixed setting parameters for different forms of respiration are, e.g., the end-expiratory pressure ($P_{PEEP}$), the inspiration time $T_i$ and the expiration time $T_e$. If a volume-controlled respiration is carried out as the first form of respiration, the first setting parameters also contain the inspiratory volume $V_T$, besides the values set as fixed values for $P_{PEEP}$, $T_i$ and $T_e$. At the time of the transition of a second form of respiration, a pressure-controlled respiration, a maximum airway pressure $P_{insp}$ must be preset. This maximum airway pressure is determined during the first form of respiration as a plateau pressure $P_{plat}$ and is taken over as a setting parameter for $P_{insp}$ during the second form of respiration. If a pressure-controlled respiration is carried out first in the reverse case, the maximum airway pressure $P_{insp}$ is preset as a setting parameter and the inspiratory volume $V_T$ is determined as a measured value during the pressure-controlled respiration. The inspiratory volume $V_T$ measured previously is taken over as a setting parameter during the volume-controlled respiration carried out subsequently. In addition to the inspiratory volume $V_T$, the mean inspiratory flow $V_{insp}$, determined as a volume per unit of time, may be determined as an additional measured variable during the pressure-controlled respiration.

The process for controlling a respirator described in the present invention consists of determining measured values for the plateau pressure $P_{plat}$ or the inspiratory volume $V_T$ by means of the measuring devices for the airway pressure and the inspiratory flow during a first form of respiration with first setting parameters and of selecting the corresponding second setting parameters at least partially from among the measured values determined during the first form of respiration at the time of changeover to a second form of respiration and of taking them over as second setting parameters for the second form of respiration.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which a preferred embodiment of the invention is illustrated.

DESCRIPTION OF THE PREFERRED EMBODIMENT

Figure 1:
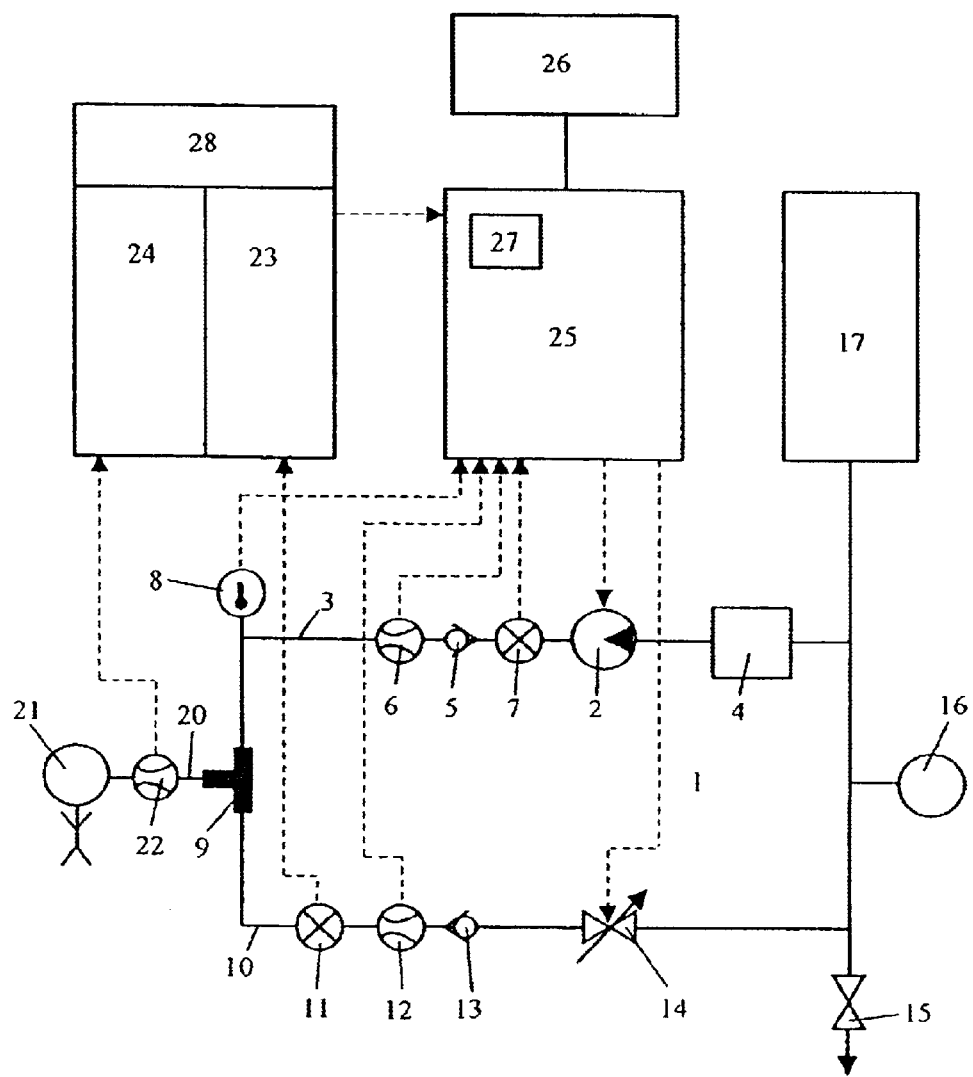
FIG. 1 is schematic diagram showing a respirator according to the present invention.

Referring to the drawings in particular, FIG. 1 schematically shows the design of a respirator 1 according to the present invention, which is adapted to the needs of anesthesia. A radial flow compressor, which is able to rapidly respond to corresponding control signals and deliver a large breathing gas volume flow due to its compact design and dynamic properties, is used as a volume-shifting device 2. A carbon dioxide absorber 4, an inspiration valve 5, a first volume flow sensor 6, a pressure sensor 7, and a temperature sensor 8 are located next to the volume-shifting device 2 in an inspiration branch 3 of the respirator 1, while the expiration branch 10, connected to the inspiration branch 3 via a Y-piece 9, contains an airway pressure sensor 11, a second volume flow sensor 12, an expiration valve 13, a controllable expiration valve 14, an excess gas discharge valve 15, and a manual respiration bag 16. Fresh breathing gas is fed from a gas-metering device 17 into the inspiration branch 3. A breathing gas flow sensor 22, which is connected to a breathing gas flow-measuring device 24, is located in a connection line 20 between a patient 21 and the Y-piece 9. The airway pressure sensor 11 is connected to an airway pressure-measuring device 23. The sensors 6, 7, 8, 12, the volume-shifting device 2, and the expiration valve 14 are connected to a control device 25, which contains a microprocessor from which all measurement, monitoring and control tasks are performed. Setting parameters for a form of respiration to be carried out by the volume-shifting device 2 are entered via an input device 26. The sensors 6, 7, 8, 12 continuously measure the pressure, the volume flow and the breathing gas temperature in the inspiration branch 3 and the expiration branch 10 and send corresponding measured values as controlled variables to the control unit 25. A comparison of the measured values with the setting parameters is performed in the control unit 25 and corresponding manipulated variables in the form of control signals are calculated for both the volume-shifting device 2 and the controllable expiration valve 14. The measured volume flow of the breathing gas is corrected by calculation in the control unit 25 in terms of the pressure and temperature effect. To do so, the pressure is continuously determined with the pressure sensor 7 and the temperature of the breathing gas is continuously determined with the temperature sensor 8 and the correction values determined.

In case of mechanical respiration, distinction is made essentially between pressure-controlled respiration and volume-controlled respiration. In case of pressure-controlled respiration, the setting parameters are usually the maximum airway pressure $P_{insp}$, the end-expiratory pressure $P_{PEEP}$, the inspiration time $T_i$ and the expiration time $T_e$. The end-expiratory pressure is set with the expiration valve 14. The expiration valve 14 is completely or partially closed during the phase of inspiration, so that the inspiratory pressure can build up in the inspiration branch 3. It is then opened during the expiration to the extent that the end-expiratory pressure $P_{PEEP}$ will become established at the end of the expiration. Instead of the inspiration time $T_i$ and the expiration time $T_e$, the respiration rate f and the ratio of the inspiration time $T_i$ to the expiration time $T_e$ is also frequently indicated instead of the inspiration time $T_i$ and the expiration time $T_e$ for the duration of one breath. The pressure rise time $T_{rampe}$ may be set as an additional setting parameter, but it does not normally have to be changed.

The inspiratory volume $V_T$ and the mean inspiratory gas flow $V_{insp}$ are dependent variables during pressure-controlled respiration, i.e., they are obtained from the value set for the maximum airway pressure $P_{insp}$. In contrast, the inspiratory volume $V_T$ is set, besides the end-expiratory pressure $P_{PEEP}$, the inspiration time $T_i$ and the expiration time $T_e$, as setting parameters in case of volume-controlled respiration, while the maximum inspiratory pressure $P_{max}$ that now becomes established as well as the plateau pressure $P_{plat}$ are the dependent variables.

The airway pressure $P_{aw}$ is continuously measured with the airway pressure sensor 11, and the airway pressure-measuring device 23 determines from this the plateau pressure $P_{plat}$, averaged over a plurality of breaths, and it sends this value to the control unit 25, where it is stored in a memory 27. The breathing gas flow sensor 22 correspondingly sends measured signals to the breathing gas flow-measuring device 24, in which an inspiratory volume $V_T$ and a mean inspiratory gas flow $V_{insp}$, obtained as a volume per unit of time, are calculated as measured values and are stored in the memory 27.

If volume-controlled respiration is set as the first form of respiration on the input unit 26, the corresponding first setting parameters are the inspiratory volume $V_T$, the end-expiratory pressure $P_{PEEP}$, the inspiration time $T_i$, and the expiration time $T_e$. The maximum airway pressure $P_{insp}$ is not active as a setting parameter during the first form of respiration, but it is continuously determined by the airway pressure-measuring device 23 and is stored in the memory 27 as a mean value averaged over a plurality of breathing strokes. Mean values for the inspiratory volume $V_T$ and the mean inspiratory gas flow $V_{insp}$, determined as a volume per unit of time, are correspondingly formed in the breathing gas flow-measuring device 24.

At the time of a changeover from the first form of respiration to the second form of respiration, which is pressure-controlled, the end-expiratory pressure $P_{PEEP}$, the inspiration time $T_i$, and the expiration time $T_e$ are taken over from the first setting parameters as second setting parameters, and the plateau pressure $P_{plat}$ measured during the first form of respiration is used as an additional setting parameter as a setting parameter for the maximum airway pressure $P_{insp}$. In such a constellation of the parameters, the patient 21 will not perceive any change caused by the changeover during the changeover from the first form of respiration to the second form of respiration, because the respiration rate, the breathing gas flow, and the airway pressure have not practically changed. Based on this stable starting value, the user then has the possibility of adapting the setting parameters in the newly set form of respiration such that optimal ventilation conditions will become established.

The conditions are different in case of a changeover from manual respiration to a mechanical form of respiration, because only the end-expiratory pressure $P_{PEEP}$ is preset during manual respiration, while the plateau pressure $P_{plat}$, the inspiratory volume $V_T$ and, if necessary, the mean inspiratory gas flow $V_{insp}$, determined as a volume per unit of time, must be determined with the measuring devices 23, 24, because they are obtained as dependent variables from the contraction of the manual breathing bag 16. The inspiration time $T_i$ and the expiration time $T_e$ are determined by a respiration time-measuring device 28 from measured curves for the airway pressure and the breathing gas flow.

Figure 2:
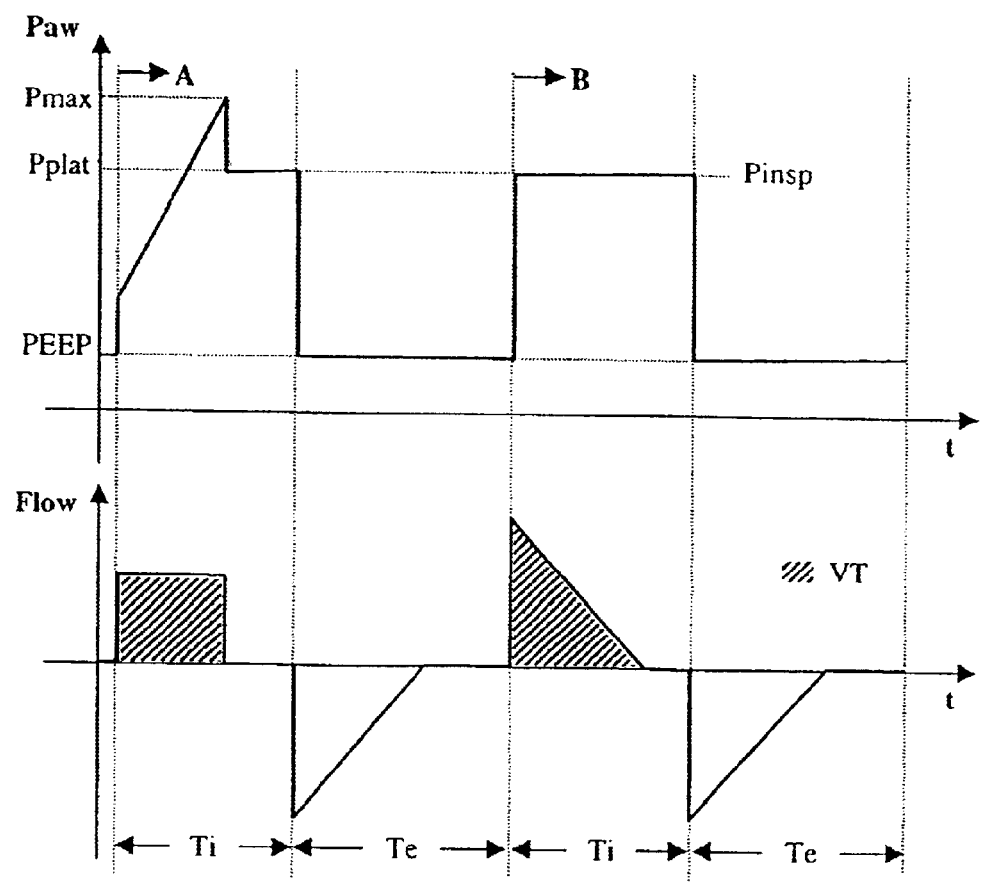
FIG. 2 are diagrams showing pressure and flow with respect to time providing a comparison of a breathing gas flow curve and a breathing gas pressure curve for volume-controlled and pressure-controlled respiration.

A comparison of the curves for the breathing gas flow and the airway pressure as a function of time is shown in FIG. 2 in an idealized form. In section "A," the respiration was carried out as volume-controlled respiration with a constant inspiratory gas flow $V_{insp}$, determined as a volume per unit of time. The shaded area in the lower curve corresponds to the area under the volume curve and indicates the inspiratory volume $V_T$. The corresponding curve of the airway pressure is shown by the upper curve in FIG. 2.

The breathing gas flow and the airway pressure during pressure-controlled respiration are shown in an idealized form in section "B" with the tidal volume as in the first (volume-controlled) respiration stroke. The maximum airway pressure $P_{insp}$ during pressure-controlled respiration corresponds to the plateau pressure $P_{plat}$ during volume-controlled respiration.

While a specific embodiment of the invention has been shown and described in detail to illustrate the application of the principles of the invention, it will be understood that the invention may be embodied otherwise without departing from such principles.

What is claimed is:

1. A respirator, comprising:
    a volume-shifting device, said volume-shifting device for carrying out preselected forms of respiration;
    a gas line system connected to said volume-shifting device for supplying a patient with breathing gas;
    measuring devices for measuring at least airway pressure and breathing gas flow, wherein at least a plateau pressure ($P_{plat}$) and an inspiratory volume ($V_T$) of the breathing gas are determined as measured values;
    a control unit, which contains an input unit for setting at least a first form of respiration and a second form of respiration as well as for entering at least first setting parameters belonging to the first form of respiration, said control unit generating control signals for at least said volume-shifting device in order to carry out the first form of respiration with the first setting parameters, said control unit being designed such that at a time of a changeover to a second form of respiration, second setting parameters are used to control the second form of respiration, said second setting parameters are selected at least partially from among the measured values determined during the first form of respiration.

2. The respirator in accordance with claim 1, wherein the volume-shifting device is a compressor actuated by a drive.

3. The respirator in accordance with claim 1, wherein an end-expiratory pressure ($P_{PEEP}$), an inspiration time ($T_i$) and an expiration time ($T_e$) are provided as common setting parameters for the first form of respiration and the second form of respiration.

4. The respirator in accordance with claim 1, wherein the first form of respiration is a volume-controlled respiration and the second form of respiration is a pressure-controlled respiration, and the first setting parameters include at least the inspiratory volume $V_T$, and at least a maximum airway pressure ($P_{insp}$), which is determined during the first form of respiration from the measured value of the plateau pressure ($P_{plat}$) by ($P_{insp}$)=($P_{plat}$), is available as one of the second setting parameters.

5. The respirator in accordance with claim 4, wherein a maximum airway pressure ($P_{insp}$) is preset as a setting parameter during pressure-controlled respiration and the inspiratory volume ($V_T$) is determined as a measured value, and that the inspiratory volume ($V_T$) determined during the pressure-controlled respiration is used as a setting parameter at the time of the changeover to the volume-controlled respiration.

6. The respirator in accordance with claim 4, wherein a mean inspiratory flow ($V_{insp}$), determined as a volume per unit of time, is determined as an additional measured variable besides the inspiratory volume ($V_T$) during the pressure-controlled respiration.

7. The respirator in accordance with claim 4, wherein a maximum inspiratory pressure ($P_{max}$) is measured in addition to or as an alternative to the plateau pressure ($P_{plat}$) during the volume-controlled respiration.

8. A respirator comprising:
a volume-shifting device for carrying out preselected forms of respiration;
a gas line system connected to said volume-shifting device for supplying a patient with breathing gas;
a manual respiration device connected to said gas line system;
measuring devices for at least measuring airway pressure, breathing gas flow and breathing time, wherein at least a plateau pressure ($P_{plat}$), an inspiratory volume ($V_T$), an inspiration time ($T_i$) and an expiration time ($T_e$) are determined as measured values;
a control unit, which contains an input unit for setting a manual form of respiration and a mechanical form of respiration with corresponding setting parameters, said control unit generating control signals for said volume-shifting device during the mechanical form of respiration in order to carry out the respiration with said setting parameters, said measured values of said inspiration time ($T_i$), said expiration time ($T_e$) and said plateau pressure ($P_{plat}$) determined during the manual form of respiration are used as said setting parameters for the mechanical form of respiration.

9. The respirator in accordance with claim 8, wherein said inspiratory volume ($V_T$) is used as a setting parameter as an alternative to said plateau pressure ($P_{plat}$).

10. A process for controlling a respirator, the respirator having a volume-shifting device for carrying out preselected forms of respiration, a gas line system connected to the volume-shifting device for supplying a patient with breathing gas and measuring devices for measuring at least airway pressure ($P_{aw}$) and breathing gas flow, wherein at least a plateau pressure ($P_{plat}$) and an inspiratory volume ($V_T$) are determined as measured values, the process comprising the steps of:
carrying out a first form of respiration with first setting parameters;
determining-the plateau pressure ($P_{plat}$) or inspiratory volume ($V_T$) measured vales, which are not first setting parameters, during the first form of respiration; and
at a time of a changeover to a second form of respiration, selecting corresponding setting parameters at least partially from among the measured values determined during the first form of respiration and taking said selected corresponding setting parameters as second setting parameters for the second form of respiration.

11. The process in accordance with claim 10, wherein said end-expiratory pressure ($P_{PEEP}$), said inspiration time ($T_i$) and said expiration time ($T_e$) are used as common setting parameters for the first form of respiration and the second form of respiration.

12. The process in accordance with claim 10, wherein the first form of respiration is carried out as volume-controlled respiration and the second form of respiration is carried out as pressure-controlled respiration, and said inspiratory volume ($V_T$) is used as the first setting parameter and a maximum airway pressure ($P_{insp}$) is used as one of the second setting parameters, wherein the maximum airway pressure ($P_{insp}$) is determined from the plateau pressure ($P_{plat}$) as a measured value during the first form of respiration.

13. The process in accordance with claim 12, wherein the maximum airway pressure ($P_{insp}$) is preset as a setting parameter during the pressure-controlled respiration and the inspiratory volume ($V_T$) is determined as a measured value, and the inspiratory volume ($V_T$) determined during the pressure-controlled respiration is used as a setting parameter at the time of the changeover to the volume-controlled respiration.

14. The process in accordance with claim 13, wherein a mean inspiratory flow ($V_{insp}$), determined as a volume per unit of time, is determined as an additional measured variable, besides said inspiratory volume ($V_t$), during the pressure-controlled respiration.

15. The process in accordance with claim 12, wherein a mean inspiratory flow ($V_{insp}$), determined as a volume per unit of time, is determined as an additional measured variable, besides said inspiratory volume $V_T$, during the pressure-controlled respiration.

16. The process in accordance with claim 12, wherein the maximum inspiratory pressure ($P_{max}$) is measured in addition or as an alternative to the plateau pressure ($P_{plat}$) during the volume-controlled respiration.

17. A process for performing a plurality of different types of respiration, the process comprising the steps of:
providing a volume-shifting device;
supplying a patient with breathing gas from the volume-shifting device through a gas line system connected to said volume-shifting device;
controlling the volume-shifting device to perform a first type of respiration;
measuring a respiration parameter from the gas line system during operation of the first type of respiration;
controlling said volume shifting device to perform a second type of respiration, said controlling of said second type of respiration including using said respiration parameter measured during the first type of respiration to control said second type of respiration.

18. A process in accordance with claim 17, wherein:
said controlling to perform the second type of respiration is performed subsequent to said controlling to perform the first type of respiration.

19. A process in accordance with claim 17, wherein:
said controlling of the first type of respiration does not use said respiration parameter.

20. A process in accordance with claim 17, wherein:
the second type of respiration is performed immediately subsequent to operation of the first type of respiration;
said controlling of the second type of respiration uses a different type of control than said controlling of the first type of respiration.

21. A process in accordance with claim 17, wherein:
the first type of respiration is manual respiration;
said measuring includes measuring tidal volume, plateau pressure, inspiration time, and expiration time;
the second type of respiration uses pressure controlled respiration;
said controlling of the second type of respiration uses said plateau pressure, said inspiration time, and said expiration time to pressure control the respiration.

22. A process in accordance with claim 21, wherein:
said controlling of the second type of respiration uses said plateau pressure as a maximum airway pressure in the pressure controlled respiration.

23. A process in accordance with claim 17, wherein:
the first type of respiration is volume controlled respiration;
said measuring includes measuring plateau pressure;
the second type of respiration is pressure controlled respiration;

said controlling of the second type of respiration uses said plateau pressure to pressure control the respiration.

24. A process in accordance with claim 23, wherein:

said controlling of the second type of respiration uses said plateau pressure as a maximum airway pressure in the pressure controlled respiration.

25. A process in accordance with claim 17, wherein:

the first type of respiration is pressure controlled respiration;

said measuring includes measuring inspiratory volume;

the second type of respiration is volume controlled respiration;

said controlling of the second type of respiration uses said inspiratory volume to volume control the respiration.

26. A process in accordance with claim 17, wherein:

the first type of respiration is manual respiration;

said measuring includes tidal volume plateau pressure, inspiration time and expiration time;

the second type of respiration is volume controlled respiration;

said controlling of the second type of respiration uses said tidal volume, said inspiration time and said expiration time to volume control the respiration.

* * * * *